(12) United States Patent
Geiger et al.

(10) Patent No.: US 10,500,043 B2
(45) Date of Patent: *Dec. 10, 2019

(54) ALIGNMENT OF AN IMPLANTABLE MEDICAL DEVICE

(71) Applicant: St. Jude Medical, Cardiology Division, Inc., St. Paul, MN (US)

(72) Inventors: Gary W. Geiger, Fridley, MN (US); Aaron J. Chalekian, Savage, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 370 days.

This patent is subject to a terminal disclaimer.

(21) Appl. No.: 15/400,210

(22) Filed: Jan. 6, 2017

(65) Prior Publication Data
US 2017/0112623 A1    Apr. 27, 2017

Related U.S. Application Data

(63) Continuation of application No. 14/445,976, filed on Jul. 29, 2014, now Pat. No. 9,566,153.
(Continued)

(51) Int. Cl.
*A61F 2/24* (2006.01)
*A61M 25/01* (2006.01)
(Continued)

(52) U.S. Cl.
CPC .......... *A61F 2/2427* (2013.01); *A61F 2/2418* (2013.01); *A61F 2/2433* (2013.01);
(Continued)

(58) Field of Classification Search
CPC ...... A61F 2/2427; A61F 2/2436; A61F 2/966; A61B 2017/003; A61B 2017/2927; A61B 1/0057; A61M 25/0147; A61M 25/0105
(Continued)

(56) References Cited

U.S. PATENT DOCUMENTS

| 3,384,088 A | 5/1968 | Miseo |
| 3,657,744 A | 4/1972 | Ersek |

(Continued)

FOREIGN PATENT DOCUMENTS

| EP | 1129744 A1 | 9/2001 |
| EP | 1157673 A2 | 11/2001 |

(Continued)

OTHER PUBLICATIONS

"Adjacent." Merriam-Webster.com. Merriam-Webster, n.d. Web. Aug. 20, 2017, 9 pages.

(Continued)

*Primary Examiner* — Katherine M Shi
(74) *Attorney, Agent, or Firm* — Lerner, David, Littenberg, Krumholz & Mentlik, LLP

(57) ABSTRACT

A medical device delivery system includes an inner shaft having a proximal end and a distal end, a support shaft having a proximal end and a distal end and an articulating assembly disposed between the inner shaft and the support shaft. The support shaft is sized for insertion into the circulatory system of a patient. The articulating assembly includes a first portion extending from the distal end of the inner shaft and a second portion at the proximal end of the support shaft. The first portion is pivotable relative to the second portion to change orientation of the support shaft relative to the inner shaft. A retainer is secured to a portion of the articulating assembly and is configured to retain a medical device on the support shaft between the retainer and the distal end of the support shaft.

20 Claims, 16 Drawing Sheets

Related U.S. Application Data

(60) Provisional application No. 61/877,107, filed on Sep. 12, 2013.

(51) Int. Cl.
| | | |
|---|---|---|
| *A61M 25/02* | (2006.01) | |
| *A61F 2/962* | (2013.01) | |
| *A61F 2/966* | (2013.01) | |
| *A61B 17/34* | (2006.01) | |

(52) U.S. Cl.
CPC .......... *A61F 2/2436* (2013.01); *A61F 2/2439* (2013.01); *A61M 25/0147* (2013.01); *A61M 25/02* (2013.01); *A61B 2017/3484* (2013.01); *A61F 2/962* (2013.01); *A61F 2/966* (2013.01); *A61F 2210/0014* (2013.01); *A61F 2220/0025* (2013.01); *A61M 2025/0293* (2013.01)

(58) Field of Classification Search
USPC ....... 606/108; 623/1.23, 2.11; 600/141, 146, 600/142, 149
See application file for complete search history.

(56) References Cited

U.S. PATENT DOCUMENTS

| | | | |
|---|---|---|---|
| 3,724,238 | A | 4/1973 | Retali et al. |
| 4,423,730 | A | 1/1984 | Gabbay |
| 4,641,657 | A | 2/1987 | Ellis |
| 5,368,592 | A | 11/1994 | Stern et al. |
| 5,372,587 | A | 12/1994 | Hammerslag et al. |
| 5,405,344 | A | 4/1995 | Williamson et al. |
| 5,507,725 | A | 4/1996 | Savage et al. |
| 5,549,594 | A | 8/1996 | Brunken |
| 5,569,270 | A | 10/1996 | Weng |
| 5,575,799 | A | 11/1996 | Bolanos et al. |
| 5,749,881 | A | 5/1998 | Sackier et al. |
| 5,843,167 | A | 12/1998 | Dwyer et al. |
| 5,868,685 | A | 2/1999 | Powell et al. |
| 5,924,424 | A | 7/1999 | Stevens et al. |
| 5,968,068 | A | 10/1999 | Dehdashtian et al. |
| 6,077,297 | A | 6/2000 | Robinson et al. |
| 6,183,432 | B1 | 2/2001 | Milo |
| 6,306,141 | B1 | 10/2001 | Jervis |
| 6,464,684 | B1 | 10/2002 | Galdonik |
| 6,623,518 | B2 | 9/2003 | Thompson et al. |
| 6,743,239 | B1 | 6/2004 | Kuehn et al. |
| 6,814,746 | B2 | 11/2004 | Thompson et al. |
| 6,830,584 | B1 | 12/2004 | Seguin |
| 7,018,406 | B2 | 3/2006 | Seguin et al. |
| 7,300,431 | B2 | 11/2007 | Dubrovsky |
| 7,311,730 | B2 | 12/2007 | Gabbay |
| 7,510,572 | B2 | 3/2009 | Gabbay |
| 7,637,905 | B2 | 12/2009 | Saadat et al. |
| 7,682,390 | B2 | 3/2010 | Seguin |
| 7,803,185 | B2 | 9/2010 | Gabbay |
| 7,811,277 | B2 | 10/2010 | Boulais |
| 9,227,990 | B2 | 1/2016 | Phull et al. |
| 2003/0050694 | A1 | 3/2003 | Yang et al. |
| 2003/0233108 | A1 | 12/2003 | Gellman et al. |
| 2004/0210304 | A1 | 10/2004 | Seguin et al. |
| 2005/0137622 | A1 | 6/2005 | Griffin |
| 2005/0137695 | A1 | 6/2005 | Salahieh et al. |
| 2005/0137697 | A1 | 6/2005 | Salahieh et al. |
| 2005/0165352 | A1 | 7/2005 | Henry et al. |
| 2005/0177138 | A1 | 8/2005 | Dubrovsky |
| 2005/0222604 | A1 | 10/2005 | Schaeffer |
| 2006/0058872 | A1 | 3/2006 | Salahieh et al. |
| 2006/0074484 | A1 | 4/2006 | Huber |
| 2006/0100687 | A1 | 5/2006 | Fahey et al. |
| 2006/0106415 | A1 | 5/2006 | Gabbay |
| 2006/0142848 | A1 | 6/2006 | Gabbay |
| 2006/0167468 | A1 | 7/2006 | Gabbay |
| 2006/0235502 | A1 | 10/2006 | Belluche et al. |
| 2006/0259120 | A1 | 11/2006 | Vongphakdy et al. |
| 2007/0010876 | A1 | 1/2007 | Salahieh et al. |
| 2007/0027534 | A1 | 2/2007 | Bergheim et al. |
| 2007/0043259 | A1 | 2/2007 | Jaffe et al. |
| 2007/0043435 | A1 | 2/2007 | Seguin et al. |
| 2007/0055358 | A1 | 3/2007 | Krolik et al. |
| 2007/0073376 | A1 | 3/2007 | Krolik et al. |
| 2007/0073391 | A1 | 3/2007 | Bourang et al. |
| 2007/0088431 | A1 | 4/2007 | Bourang et al. |
| 2007/0112422 | A1 | 5/2007 | Dehdashtian |
| 2007/0162100 | A1 | 7/2007 | Gabbay |
| 2007/0168013 | A1 | 7/2007 | Douglas |
| 2007/0203575 | A1 | 8/2007 | Forster et al. |
| 2007/0239271 | A1 | 10/2007 | Nguyen |
| 2007/0244552 | A1 | 10/2007 | Salahieh et al. |
| 2007/0250113 | A1 | 10/2007 | Hegeman et al. |
| 2008/0065122 | A1 | 3/2008 | Stack et al. |
| 2008/0071369 | A1 | 3/2008 | Tuval et al. |
| 2008/0147160 | A1 | 6/2008 | Ghione et al. |
| 2008/0147182 | A1 | 6/2008 | Righini et al. |
| 2008/0228223 | A1 | 9/2008 | Alkhatib |
| 2009/0054975 | A1 | 2/2009 | del Nido et al. |
| 2009/0062606 | A1 | 3/2009 | Ueda et al. |
| 2009/0062839 | A1 | 3/2009 | Kurrus |
| 2010/0004740 | A1 | 1/2010 | Seguin et al. |
| 2010/0057000 | A1 | 3/2010 | Melsheimer et al. |
| 2010/0204708 | A1 | 8/2010 | Sharma |
| 2010/0228152 | A1 | 9/2010 | Fisher et al. |
| 2010/0228191 | A1 | 9/2010 | Alvarez et al. |
| 2010/0286768 | A1 | 11/2010 | Alkhatib |
| 2010/0298931 | A1 | 11/2010 | Quadri et al. |
| 2011/0098800 | A1 | 4/2011 | Braido et al. |
| 2011/0207999 | A1 | 8/2011 | Torisawa et al. |
| 2011/0224678 | A1 | 9/2011 | Gabbay |
| 2011/0245917 | A1 | 10/2011 | Savage et al. |
| 2012/0078350 | A1 | 3/2012 | Wang et al. |
| 2012/0303111 | A1 | 11/2012 | Dwork et al. |
| 2013/0060328 | A1 | 3/2013 | Rothstein |
| 2013/0103047 | A1 | 4/2013 | Steingisser et al. |
| 2013/0274870 | A1 | 10/2013 | Lombardi et al. |
| 2013/0297012 | A1* | 11/2013 | Willard ................. A61F 2/2436 623/2.11 |
| 2013/0297102 | A1 | 11/2013 | Hughes et al. |

FOREIGN PATENT DOCUMENTS

| | | |
|---|---|---|
| EP | 1716822 A1 | 11/2006 |
| EP | 1926455 A2 | 6/2008 |
| FR | 2765098 A1 | 12/1998 |
| WO | 9510317 A1 | 4/1995 |
| WO | 2006138173 A2 | 12/2006 |
| WO | 07071436 A2 | 6/2008 |
| WO | 08070797 A2 | 6/2008 |
| WO | 10051025 A1 | 5/2010 |
| WO | 10087975 A1 | 8/2010 |
| WO | 2010127162 A1 | 11/2010 |
| WO | 2012112469 A2 | 8/2012 |
| WO | 2013166355 A1 | 11/2013 |
| WO | 2014130160 A1 | 8/2014 |

OTHER PUBLICATIONS

International Search Report and Written Opinion for Application No. PCT/US2014/054025 dated Nov. 19, 2014.

International Search Report and Written Opinion for Application No. PCT/US2014/055053 dated Nov. 24, 2014.

Ruiz, Carlos, Overview of PRE-CE Mark Transcatheter Aortic Valve Technologies, Euro PCR, May 25, 2010.

Quaden, Rene, et al., Percutaneous aortic valve replacement: resection before implantation, 836-840,European J. of Cardio-thoracic Surgery, 27 (2005).

International Search Report for Application No. PCT/US2013/078306 dated May 2, 2014.

International Search Report and Written Opinion for Application No. PCT/US2013/039405 dated Sep. 23, 2013.

U.S. Appl. No. 13/790,132, filed Mar. 3, 2013.

(56) References Cited

OTHER PUBLICATIONS

U.S. Appl. No. 15/004,373, filed Jan. 22, 2016.

* cited by examiner

100

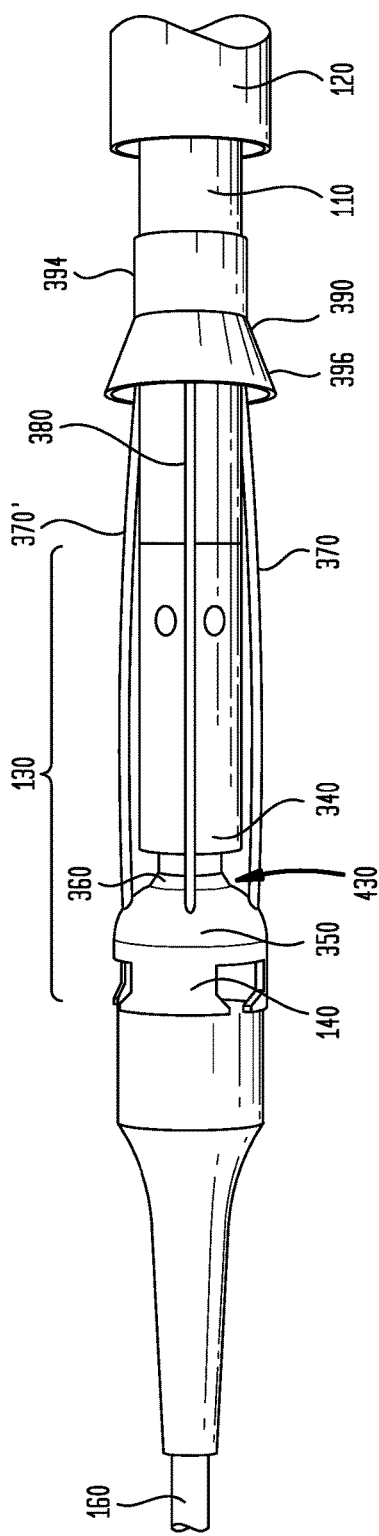
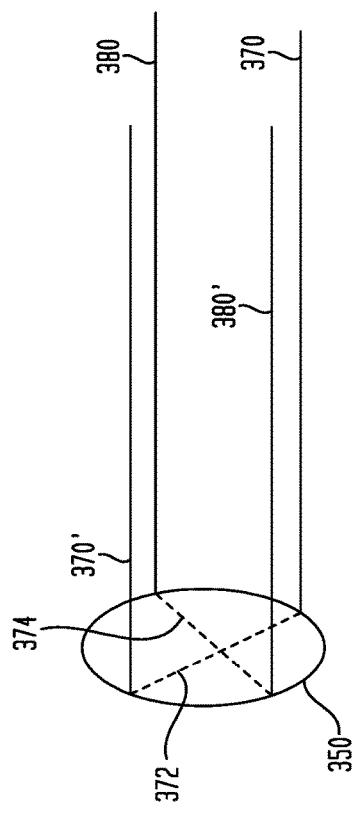
FIG. 3A
FIG. 3B

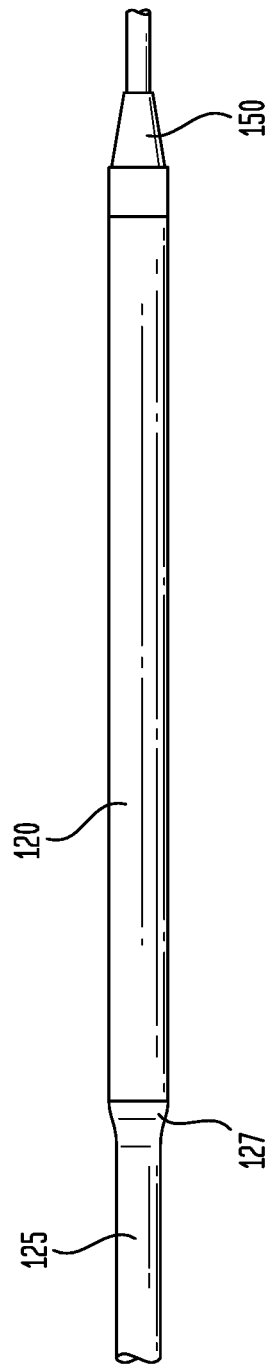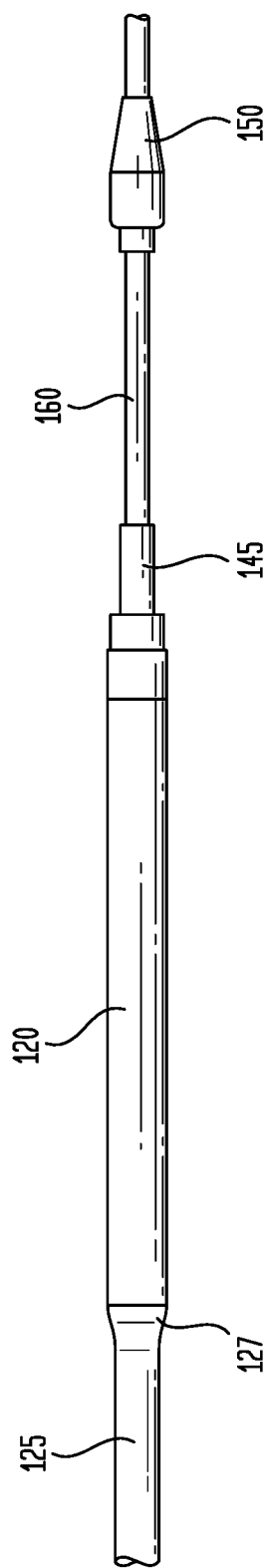

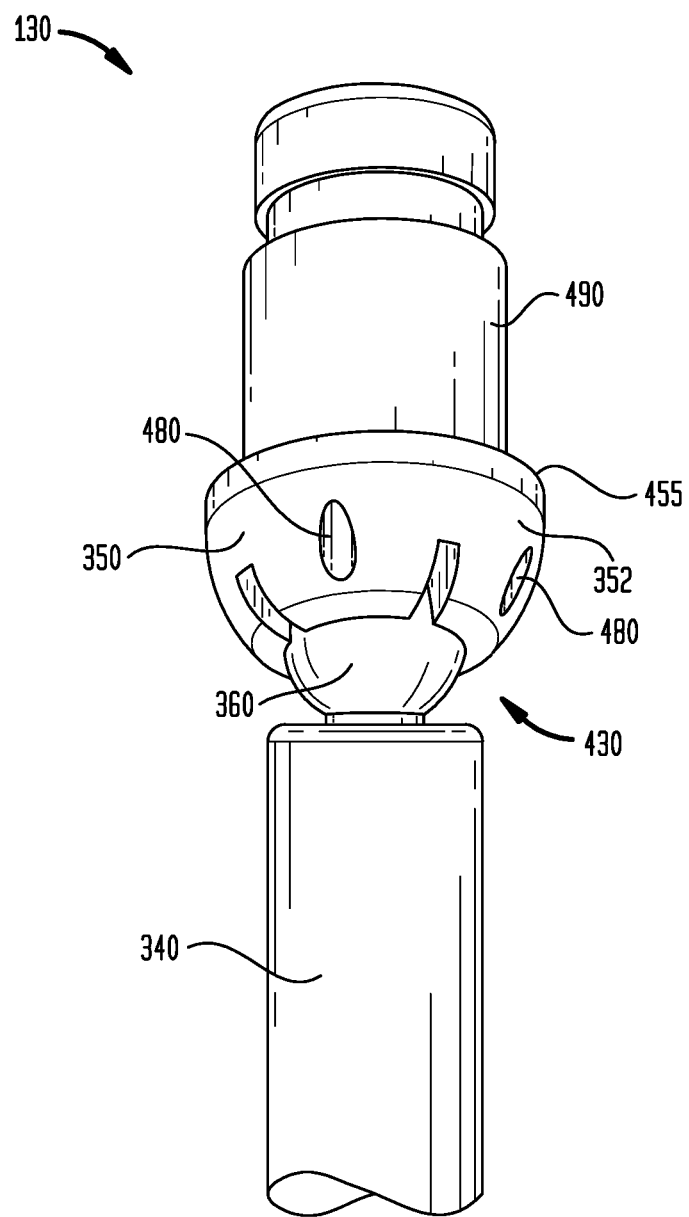

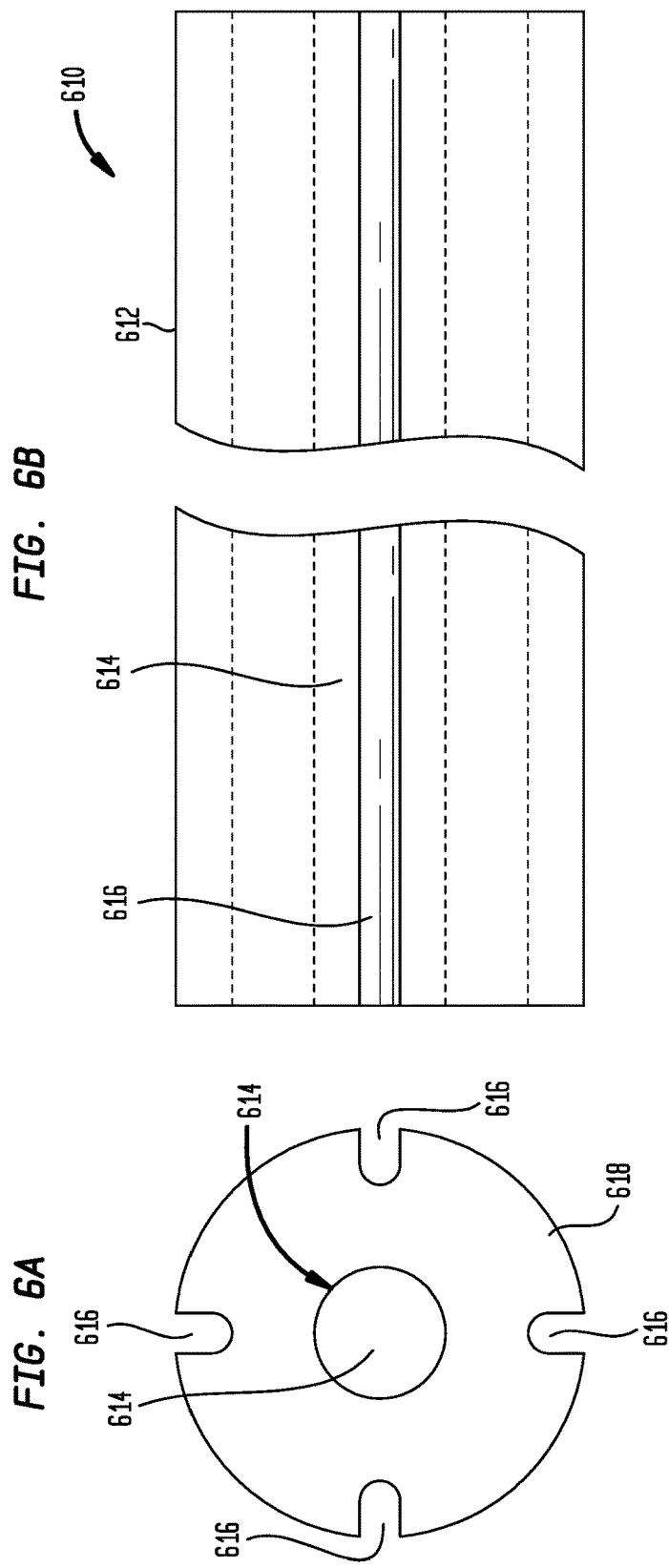

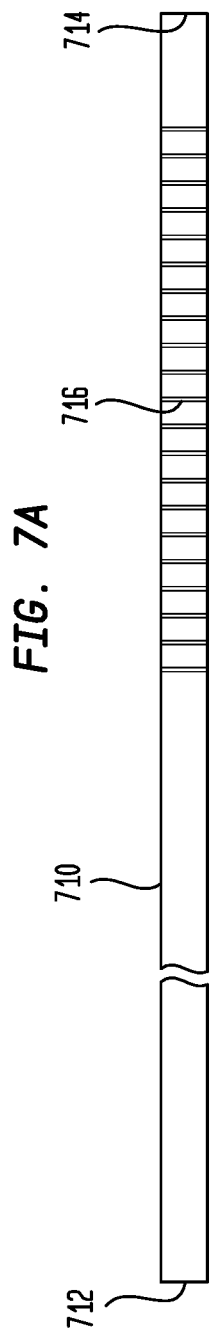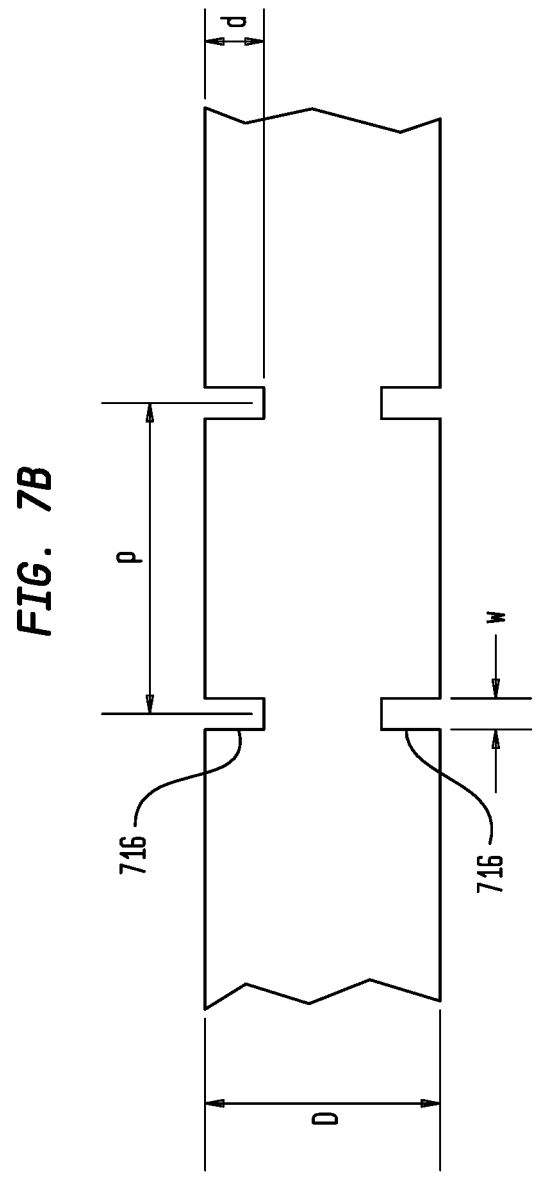

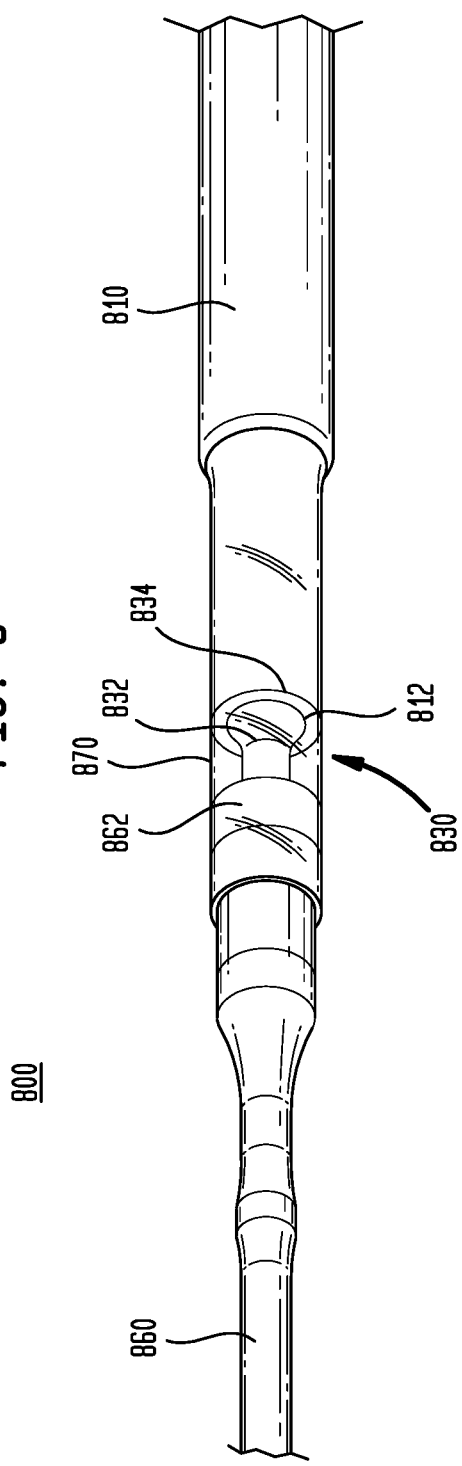

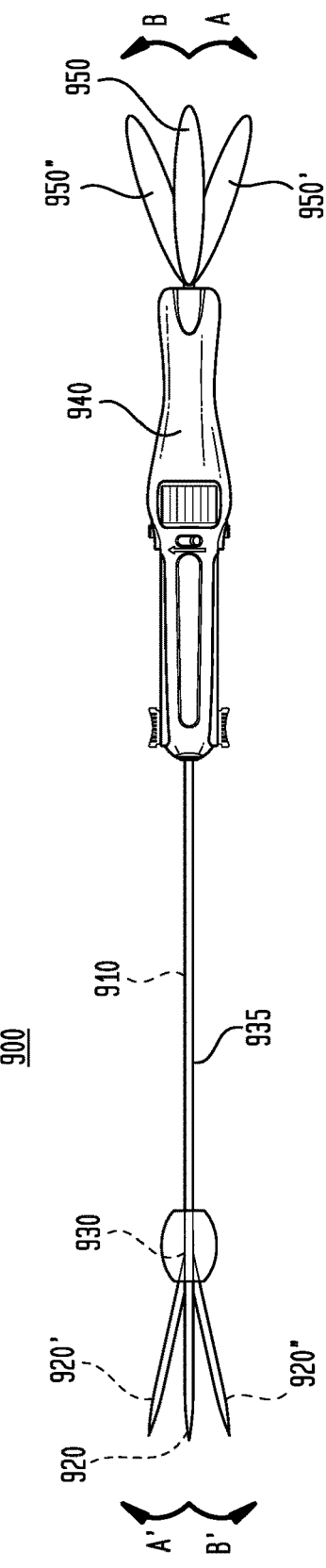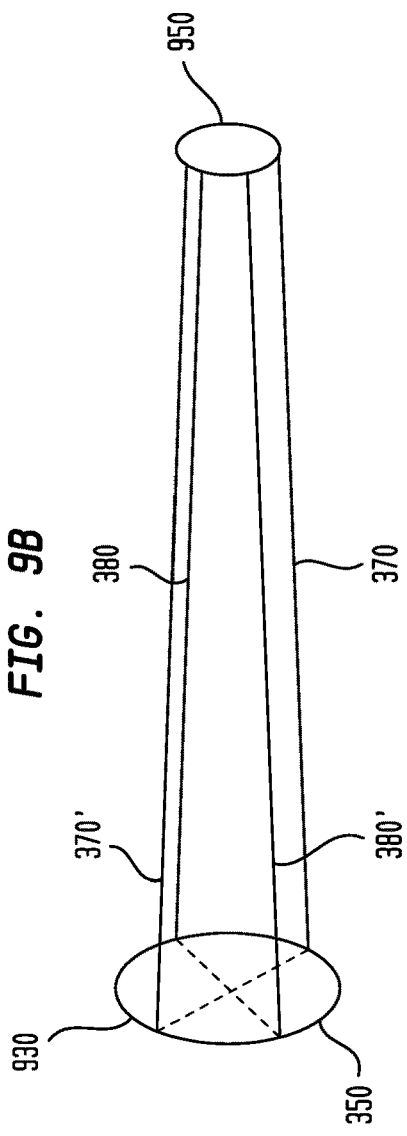

12;

ALIGNMENT OF AN IMPLANTABLE MEDICAL DEVICE

CROSS-REFERENCE TO RELATED APPLICATIONS

This application is a continuation of U.S. application Ser. No. 14/445,976, filed on Jul. 29, 2014, which claims the benefit of the filing date of the U.S. Provisional Patent Application No. 61/877,107, filed on Sep. 12, 2013, the disclosures of which are hereby incorporated herein by reference.

BACKGROUND OF THE INVENTION

The present disclosure relates in general to heart valve replacement and, in particular, to collapsible prosthetic heart valves. More particularly, the present disclosure relates to devices and methods for positioning collapsible prosthetic heart valves within a native annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size.

BRIEF SUMMARY OF THE INVENTION

An embodiment according to the present disclosure includes a medical device delivery system with an inner shaft having a proximal end and a distal end, a support shaft having a proximal end and a distal end and an articulating assembly disposed between the inner shaft and the support shaft. The support shaft is sized for insertion into the circulatory system of a patient. The articulating assembly includes a first portion at the distal end of the inner shaft and a second portion at the proximal end of the support shaft. The first portion is pivotable relative to the second portion to change orientation of the support shaft relative to the inner shaft.

Another embodiment according to the present disclosure includes a support shaft configured to retain a medical device in a collapsed condition and having a proximal end and a distal end, an inner shaft having a proximal end and a distal end, an articulating assembly disposed between the support shaft and the inner shaft, a handle disposed proximally of the inner shaft, an actuator mechanism pivotably secured to the handle and a plurality of control wires operatively interconnecting the articulating assembly and the actuator mechanism such that pivoting movement of the actuator mechanism causes a corresponding movement of the support shaft relative to the inner shaft.

BRIEF DESCRIPTION OF THE DRAWINGS

Various embodiments of the present disclosure will now be described with reference to the appended drawings. It is to be appreciated that these drawings depict only some embodiments of the disclosure and are therefore not to be considered limiting of its scope.

FIG. 3A is an enlarged side elevational view of an articulating assembly for use in the delivery system of FIG. 1 according to another embodiment of the disclosure;

FIG. 3B is a highly schematic view of a socket and four control wires of the articulating assembly of FIG. 3A;

FIG. 3C is a side elevational view of an outer sheath covering the articulating assembly and an inner support shaft of the delivery system of FIG. 3A;

FIG. 3D is a side elevational view of the outer sheath of FIG. 3C moved relative to the inner support shaft for deploying the medical device;

FIG. 4 is an enlarged front elevational view of the articulating assembly of FIG. 3A;

FIG. 6A is an end view of another inner shaft of a delivery system;

FIG. 6B is a front elevational view of the inner shaft of FIG. 6A;

FIG. 7A is a side elevational view of a further inner shaft of a delivery system;

FIG. 7B is an enlarged detailed view of a section of the inner shaft of FIG. 7A;

FIG. 8 is a side perspective view of an articulating assembly for use in a delivery system according to a still further embodiment of the disclosure;

FIG. 9A is a schematic illustration of a delivery system including an articulating support shaft and an actuator mechanism for manipulating the support shaft according to an embodiment of the disclosure;

FIG. 9B is a highly schematic illustration of four control wires associated with the support shaft and the actuator mechanism of FIG. 9A;

DETAILED DESCRIPTION

Despite the various improvements that have been made to the collapsible prosthetic heart valve delivery process, conventional devices suffer from some shortcomings. For example, with conventional self-expanding valves, the clinical success of the valve is dependent on accurate deployment and anchoring. Inaccurate deployment and anchoring of the valve increases risks, such as those associated with valve migration. Inaccurate deployment and anchoring may also result in the leakage of blood between the implanted heart valve and the native valve annulus, commonly referred to as paravalvular leakage (also known as "perivalvular leakage"). In aortic valves, this leakage enables blood to flow from the aorta back into the left ventricle, reducing cardiac efficiency and putting a greater strain on the heart muscle.

There, therefore, is a need for further improvements to the devices, systems, and methods for positioning and deploying collapsible prosthetic heart valves. Specifically, there is a need for further improvements to the devices, systems, and methods for accurately implanting a prosthetic heart valve. For instance, it is desirable to position the prosthetic valve precisely within the native anatomy to achieve optimal results. Furthermore, it may be desirable to reduce or minimize the effort and time spent by a user to achieve the precise positioning of the prosthetic valve. Among other advantages, the present disclosure may address one or more of these needs. More particularly, various embodiments of alignment elements may assist a user to precisely position the prosthetic valve while reducing the effort and time spent by the user.

When used in connection with devices for delivering a prosthetic heart valve or other medical device into a patient, the terms "proximal" and "distal" are to be taken as relative to the user of the delivery devices. "Proximal" is to be understood as relatively close to the user, and "distal" is to be understood as relatively farther away from the user. Also, as used herein the terms "substantially," "generally," and "about" are intended to mean that slight deviations from absolute are included within the scope of the term so modified.

Figure 1:
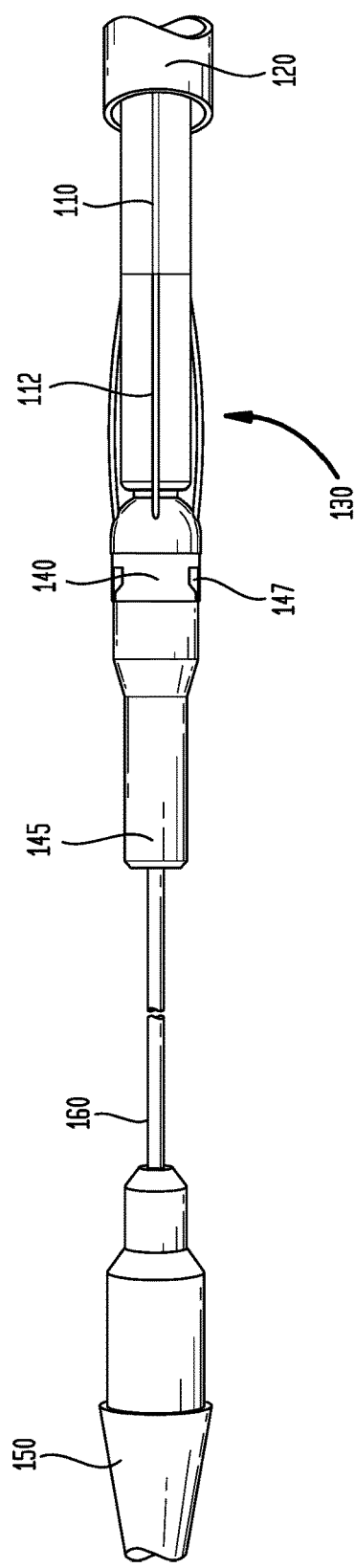
FIG. 1 is a side elevational view of the distal end of a delivery system for delivering a medical device according to one embodiment of the disclosure.

Referring now to the figures, FIG. 1 illustrates delivery system 100 for delivering a medical device according to an embodiment of the disclosure. Delivery system 100 includes inner shaft 110 having distal end 112, and distal outer tubular sheath 120 slideably disposed around the inner shaft. Articulating assembly 130 is arranged at distal end 112 of inner shaft 110 between the inner shaft and retainer 140. Retainer 140 includes a generally cylindrical body 145 extending distally therefrom. Support shaft 160 extends distally from retainer 140, through body 145 to conically shaped distal tip 150 of delivery system 100. A collapsible medical device, for example, a collapsible prosthetic heart valve with a self-expanding stent or a balloon expandable stent (not shown), may be loaded into delivery system 100 between distal tip 150 and retainer 140. The medical device may be at least partly supported by body 145, and held in a collapsible condition by distal outer sheath 120. In an exemplary embodiment, retainer 140 includes a plurality of recesses 147 for accommodating retention elements (not shown) formed on the stent of the medical device.

In a closed position (similar to FIG. 3C), distal outer sheath 120 is configured to cover inner shaft 110, articulating assembly 130, support shaft 160 and a medical device positioned about support shaft 160 between retainer 140 and distal tip 150. The distal end of distal outer sheath 120 may extend over a reduced diameter position of distal tip 150 to prevent fluid entering outer sheath 120 during the delivery of the medical device to a desired location in a patient's anatomy. Once the medical device has reached the desired location, distal outer sheath 120 may be pulled proximally relative to distal tip 150 to an open position, illustrated in FIG. 1, thereby uncovering the medical device. The exposed medical device, for example, a self-expanding prosthetic heart valve, may then expand to a deployed configuration.

Figure 2:
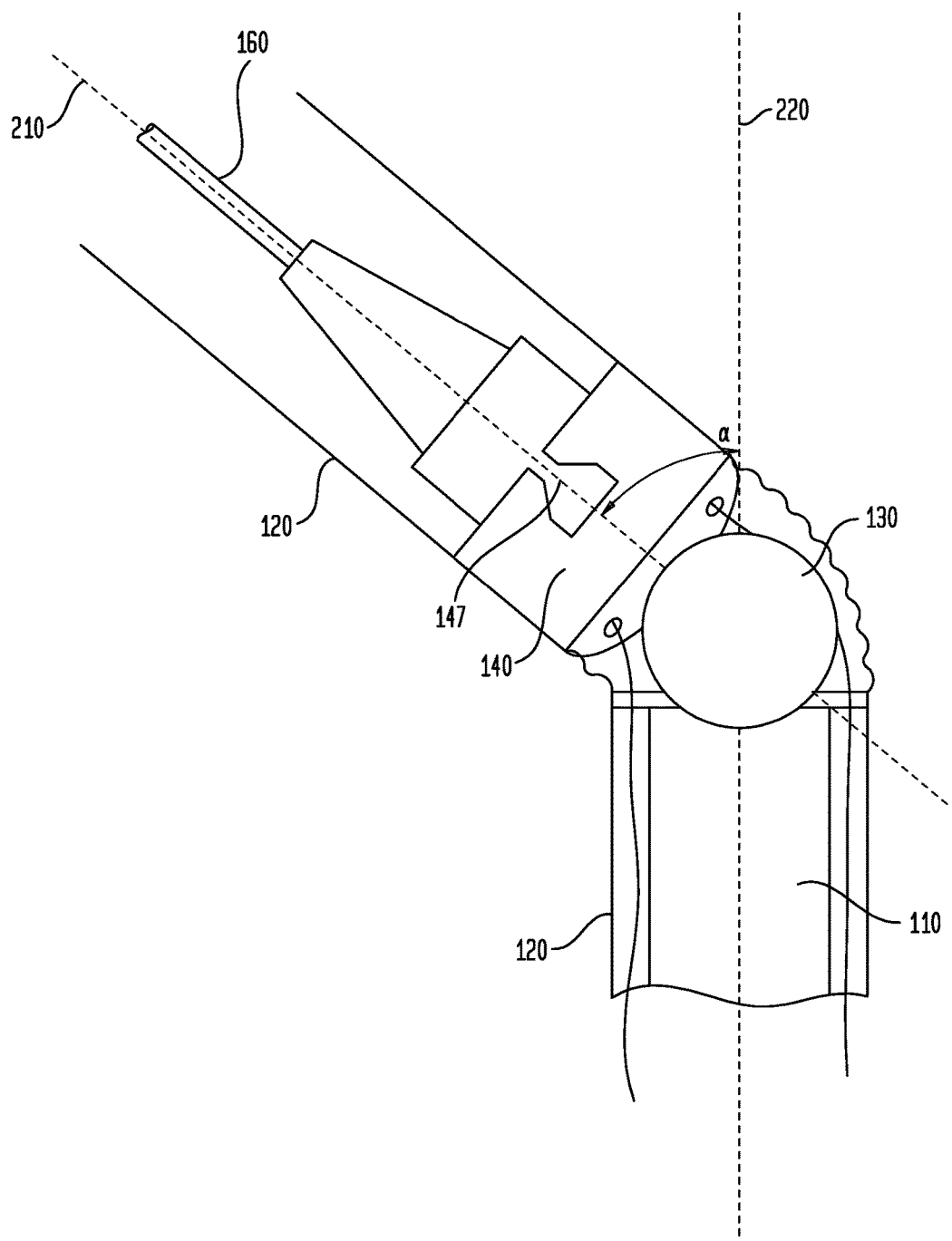
FIG. 2 is an enlarged side elevational view of an articulating assembly for use in the delivery system of FIG. 1 according to one embodiment of the disclosure.

Referring now to FIG. 2, articulating assembly 130 is illustrated in greater detail. Articulating assembly 130 connects support shaft 160 to inner shaft 110, and, as will be explained in further detail below, enables support shaft 160, along with retainer 140, distal tip 150, and the medical device mounted therebetween, to articulate to a desired angle relative to inner shaft 110. More particularly, articulating assembly 130 enables support shaft 160 to move relative to inner shaft 110 so that longitudinal axis 210 of support shaft 160 is at an angle α relative to longitudinal axis 220 of inner shaft 110. Angle α may be between about 0° and about 45°. As a result, articulating assembly 130 improves the trackability of delivery system 100, and, in particular, support shaft 160 and the associated medical device, along the aortic arch and other portions of the patient's cardiovascular system.

With reference to FIGS. 3A-3D, articulating assembly 130 includes hollow connector 340 affixed on distal end 112 of inner shaft 110, with a spherical ball 360 projecting from the distal end of the connector. A complementary socket 350 is formed in the proximal end of retainer 140. Spherical ball 360 is assembled in socket 350 to form a ball and socket joint 430 that is pivotable in all directions. Since ball and socket joints are known in the art, they are not described in further detail for sake of brevity.

Distal outer tubular sheath 120 is illustrated as covering articulating assembly 130 as well as the support shaft 160 in FIG. 3C. On the other hand, FIG. 3D illustrates distal outer tubular sheath 120 moved proximally, thereby exposing support shaft 160, for example, for deploying the medical device supported by the support shaft, when the delivery system has been positioned in the anatomy of a patient or for installing a medical device on the support shaft 160 before the delivery system is used to deploy the medical device. Distal outer sheath 120 is connected to a proximal outer sheath 125 via a transition segment 127. Distal outer sheath 120 has a first diameter sufficiently large to accommodate and constrain a medical device supported by support shaft 160 as well as to cover the articulating assembly. Proximal outer sheath 125 has a second diameter, generally smaller than the first diameter, sized to accommodate inner shaft 110. Thus, a distal end of transition segment 127 has a diameter equal to the first diameter and a proximal end of the transition segment has a diameter equal to the second diameter.

Control wires 370, 370', 380, and 380' (only wires 370, 370', 380 are visible in FIG. 3A) are connected at one end to retainer 140 and extend proximally along inner shaft 110 to a handle (not shown) at the proximal end of delivery system 100. Preferably, control wires 370, 370', 380, and 380' are disposed substantially symmetrically about retainer 140 and inner shaft 110 so that wire 370' is diametrically opposed to wire 370, and wire 380' is diametrically opposed to wire 380, all as illustrated in FIG. 3B. Thus, control wires 370 and 370' lie in a first plane 372, and control wires 380 and 380' lie in a second plane 374 substantially perpendicular to the first plane. Accordingly, each one of control wires 370, 370', 380, and 380' is spaced from an adjacent control wire by about 90° in the circumferential direction of retainer 140 and inner shaft 110. It will, of course, be understood that other embodiments of the articulating assembly may include more than or less than four control wires depending on the requirements of a given application. Still further, other embodiments may include control wires asymmetrically disposed about retainer 140 and inner shaft 110.

Control wires 370, 370', 380 and 380' may be held near or against inner shaft 110 by constricting member 390 disposed for sliding movement along the inner shaft. Constricting member 390 further engages control wires 370, 370', 380, and 380' such that the control wires are free to move longitudinally relative to the constricting member and to inner shaft 110. Constricting member 390 has a generally cylindrical proximal portion 394, which is secured to inner shaft 110 and which acts as a guide to constrain control wires 370, 370', 380, 380' when used with a slotted inner member (for example, as illustrated in FIGS. 6A and 6B). Constricting member 390 further includes a distal portion 396 tapering outwardly toward its distal end. Outwardly tapered portion 396 of constricting member 390 has a geometry generally similar to that of transition segment 127 between distal outer tubular sheath 120 and proximal outer sheath 125. Outwardly tapered portion 396 serves as a backstop to prevent possible damage to articulating assembly 130 and control wires 370, 370', 380, 380' extending therefrom due to a potential contact with the smaller sized proximal outer sheath 125 during a relative longitudinal movement of the outer sheaths 120, 125 and inner shaft 110.

In the embodiment illustrated in FIGS. 3A-3D, a user may control the direction and extent of the deviation of support shaft 160 relative to inner shaft 110 by using a handle actuator (not shown). For instance, pulling control wire 370 proximally would cause the bottom of retainer 140 (as seen in FIGS. 3A and 3B) to pivot on ball 360 toward the handle of the delivery system. At the same time, the pivoting of retainer 140 will pull opposite control wire 370' distally. Consequently, support shaft 160 will articulate in a downward direction relative to inner shaft 110.

On the other hand, pulling control wire 380 proximally would cause the front of retainer 140 (as seen in FIGS. 3A and 3B) to pivot on ball 360 toward the handle. As control wire 380 is pulled proximally, the pivoting of retainer 140 will pull opposite control wire 380' distally, with the result of pivoting support shaft 160 outward from the plane of the paper relative to inner shaft 110. Thus, in the exemplary embodiment illustrated in FIGS. 3A and 3B, four control wires 370, 370', 380 and 380' provide four principal directions of articulation of support shaft 160 relative to inner shaft 110. Furthermore, pulling any two adjacent control wires proximally simultaneously would cause support shaft 160 to articulate relative to inner shaft 110 in a direction between the two corresponding principal directions affected by the control wires. It will be appreciated that support shaft 160 may be articulated to the same position in steps rather than directly by the sequential operation of the same control wires.

Referring now to FIG. 4, ball and socket joint 430 of articulating assembly 130 is illustrated in further detail. Articulating assembly 130 includes connector 340 with spherical ball 360 projecting from the distal end thereof. Ball 360 is assembled for pivoting movement in all directions in complementary socket 350 formed in generally hemispherically-shaped portion 352 of another connector 490 connected to the proximal end of support shaft 160. Although not shown in FIG. 4, connector 490 may include retainer 140 distal to hemispherically-shaped portion 352. A plurality of apertures 480 may be spaced around the circumference of portion 352. Apertures 480 are configured to receive control wires 370, 370', 380 and 380'. Connector 490 is configured to pivot relative to ball 360 responsive to the movement of one or more of the control wires, as described above. As connector 490 pivots relative to ball 360, support shaft 160 and the medical device mounted about same will articulate relative to inner shaft 110.

Figure 5B:
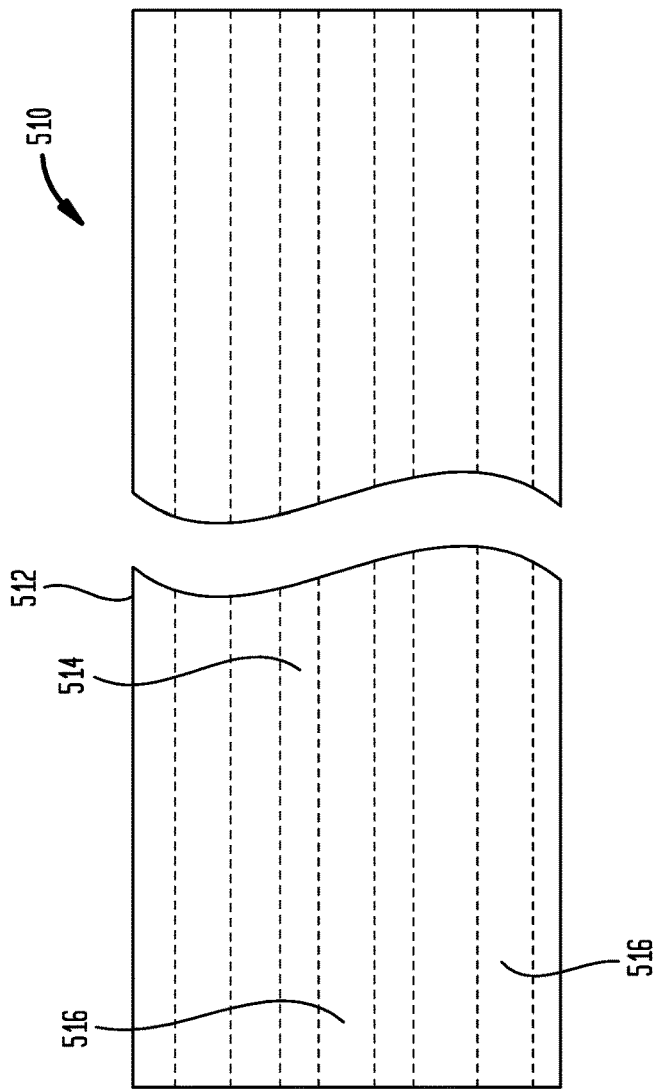
FIG. 5B is a front elevational view of the inner shaft of FIG. 5A.
Figure 5A:
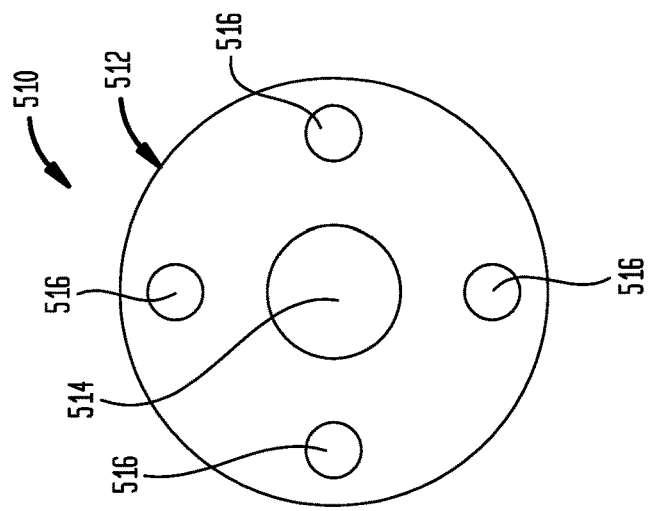
FIG. 5A is an end view of an inner shaft of a delivery system.

In the description above, control wires 370, 370', 380, and 380' extend along the exterior of inner shaft 110 toward the handle of delivery system 100. FIGS. 5A-5B illustrate inner shaft 510 according to another embodiment of the disclosure which accommodates the control wires internally thereof. Inner shaft 510 comprises a generally tubular body 512 having central lumen 514 and a plurality of peripheral lumens 516. Central lumen 514 is configured to accommodate a guide wire (not shown) that may extend through the delivery system from the handle and out through the distal tip thereof. Peripheral lumens 516 are configured to accommodate control wires (not shown), such as, for example, control wires 370, 370', 380, and 380', for sliding movement through inner shaft 510. Thus, the control wires may be pulled or pushed longitudinally through peripheral lumens 516. It will be understood that, while inner shaft 510 in the illustrated embodiment includes four peripheral lumens 516, other embodiments of the inner shaft may include more or less than four peripheral lumens depending on the number of control wires in the delivery system.

Inner shaft 610 according to a further embodiment of the disclosure is illustrated in FIGS. 6A-6B. Inner shaft 610 comprises a generally tubular body 612 having central lumen 614 and a plurality of peripheral slots 616 defined in outer surface 618 of the tubular body. Central lumen 614 is configured to accommodate a guide wire (not shown) that may extend through the delivery system from the handle and out through the distal tip thereof. Peripheral slots 616 are configured to accommodate control wires (not shown), such as for example, control wires 370, 370', 380, and 380', for sliding movement relative to inner shaft 610. Thus, the control wires may be pulled or pushed longitudinally through peripheral slots 616. It will be understood that, while inner shaft 610 in the illustrated embodiment includes four peripheral slots 616, other embodiments of the inner shaft may include more or less than four peripheral slots depending on the number of control wires in the delivery system. A constricting member, such as constricting member 390, may be used to ensure that control wires 370, 370', 380, and 380' are retained within corresponding peripheral slots 616.

Referring now to FIGS. 7A-7B, inner shaft 710 according to yet another embodiment of the disclosure is illustrated. Inner shaft 710 has a length between proximal end 712 and distal end 714, and includes a plurality of notches 716 along at least a portion of its length. In an exemplary arrangement, notches 716 may be formed along a distal portion of inner shaft 710. Inner shaft 710 may have a circular cross-section with a diameter D, and each notch 716 may be formed with a depth d from the outer surface of the inner shaft and a width w in the length direction thereof. In a non-limiting configuration, inner shaft 710 may have a diameter D of about 0.118 inch and each notch 716 may have a depth d of about 0.015 inch and a width w of about 0.01 inch. Notches 716 may be identical to one another, and may extend around the entire circumference of inner shaft 710. Notches 716 may be spaced from one another in the length direction of inner shaft 710 by a pitch p, which may be substantially uniform along the length of the inner shaft. In an exemplary configuration, the pitch p of notches 716 may be about 0.1 inch. The presence of notches 716 along a distal portion of inner shaft 710 makes the inner shaft relatively more flexible near its distal end than near its proximal end. Such flexibility of a distal segment of inner shaft 710 may assist in better navigating the delivery system through various curved contours of the patient's anatomy without sacrificing the structural integrity of the delivery system significantly.

In an exemplary embodiment, the ratio of depth d of notches 716 to diameter D of inner shaft 710 may be between about 0.1 and about 0.15. Likewise, the ratio of a width w of notches 716 to diameter D may be between about 0.06 and about 0.1. Depending on the requirements of a given application, these ratios may have different values without departing from the scope of the disclosure.

It will further be understood that other embodiments of the inner shaft may have different geometric cross-sections such as oval, square, and polygonal. Still further, other embodiments of the inner shaft may have different ratios of notch depth and width to shaft diameter. If the cross-section of the inner shaft is other than circular, then the diameter D represents the major dimension of the given shape. In yet other embodiments of the inner shaft, the notches may extend only partially around the circumference of the inner shaft. Likewise, in some embodiments, one or more of the notches may differ from the others in one or both of their widths and depths, and may be spaced apart from one another by different pitches. Combinations of the various features discussed above may be implemented in a single embodiment of the inner shaft all, of which are deemed to be within the scope of the present disclosure.

In other embodiments, the articulating assembly may take the form of a passive assembly that responds to resistance encountered by distal tip 150 as the delivery system is advanced through the patient's anatomy, and enables support shaft 160 to articulate relative to inner shaft 110. FIG. 8 illustrates a section of delivery system 800 according to an embodiment of the disclosure. Delivery system 800 includes proximal shaft 810 having a distal end 812 and support shaft 860 having proximal end 862. Articulating assembly 830 pivotably connects distal end 812 of proximal shaft 810 to proximal end 862 of support shaft 860. Articulating assembly 830 includes a spherical ball 832 that extends proximally from proximal end 862 of support shaft 860. Distal end 812 of proximal shaft 810 has a generally concave end surface 834 that acts as a bearing surface for pivotal movement of ball 832. Sheath 870 covers articulating assembly 830 as well as at least a portion of proximal shaft 810 and support shaft 860. Sheath 870 frictionally engages proximal shaft 810 and support shaft 860 so as to longitudinally constrain ball 832 relative to concave end surface 834 such that there is no longitudinal movement or separation therebetween. However, since ball 832 is pivotable relative to concave end surface 834, support shaft 860 may articulate relative to the longitudinal axis of proximal shaft 810 in a manner similar to that illustrated in FIG. 2.

FIGS. 9A and 9B illustrate a delivery system 900 according to an embodiment of the disclosure. Delivery system 900 includes an inner shaft shown in phantom as 910, support shaft shown in phantom as 920, and an articulating assembly shown in phantom as 930 secured therebetween, underneath catheter 935. Handle 940 is provided at the proximal end of inner shaft 910. An actuator mechanism 950 is attached to handle 940. In an exemplary embodiment, articulating assembly 930 may take the form of a ball and socket joint as illustrated in FIGS. 3A and 3B, or any of the articulating assemblies described herein. Four control wires 370, 370', 380, and 380' extend from articulating assembly 930 to handle 940 and actuator mechanism 950.

As schematically illustrated in FIG. 9B, the distal ends of four control wires 370, 370', 380, and 380' are ultimately secured to support shaft 920 (for example, via a retainer and socket similar to those illustrated in FIGS. 3A and 3B). The proximal ends of control wires 370, 370', 380, and 380' are secured to actuator mechanism 950 such that pivoting movement of actuator mechanism 950 relative to handle 940 causes at least one of the control wires to be pulled proximally, thereby urging support shaft 920 to articulate in a corresponding direction relative to inner shaft 910.

For instance, if actuator mechanism 950 is pivoted downwardly in the direction indicated by arrow A to the position illustrated in phantom at 950' in FIG. 9A, support shaft 920 will articulate upwardly relative to inner shaft 910 in the direction indicated by arrow A' and assume the position illustrated in phantom at 920'. When actuator mechanism 950 is so pivoted, a control wire, for example, control wire 370' of FIG. 9B, will be pulled proximally, thereby urging support shaft 920 in an upward direction. If actuator mechanism 950, on the other hand, is pivoted upwardly in the direction indicated by arrow B to the position illustrated in phantom at 950" in FIG. 9A support shaft 920 will articulate downwardly relative to inner shaft 910 in the direction shown by arrow B' and assume the position illustrated in phantom at 920". For sake of simplicity, only two-dimensional movements of actuator mechanism 950 and support shaft 920 are described herein. It will be understood that actuator mechanism 950 may also be pivoted in directions orthogonal or transverse to the directions indicated by arrows A and B, thereby enabling articulating assembly 930 and support shaft 920 to move in corresponding three-dimensional articulating directions relative to inner shaft 910.

Referring now to FIGS. 10A-10D, one embodiment of an actuator mechanism 1000 for a delivery system having any one of the articulating assemblies described above is illustrated. In the illustrated embodiment, actuator mechanism 1000 employs a ball and socket joint, as described in detail below, such that actuator mechanism 1000 may be manipulated relative to handle 1070 of the delivery system. Actuator mechanism 1000 includes a ball 1010 having a stem that is fixedly connected to the proximal end of handle 1070 by a mounting ring 1060. The spherical portion of ball 1010 is mounted in a housing 1020 so that the housing can pivot in any direction relative to handle 1070. Housing 1020 may include a first portion 1022 and a second portion 1024 secured to one another by fasteners 1030 and 1040 so as to capture ball 1010 therebetween. Locking ring 1050 tightens housing portions 1022, 1024 around ball 1010. In an exemplary configuration, locking ring 1050 may include a thumbscrew or other tightenable fastener for adjusting the pressure exerted by the locking ring on housing portions 1022, 1024. As the fastener is tightened, increased friction created between ball 1010 and housing 1020 will constrain the pivoting movement of the housing relative to the ball so as to retain actuator mechanism 1000 in a desired position relative to handle 1070 and, in turn, the desired orientation of the support shaft relative to the inner shaft.

Figure 10A:
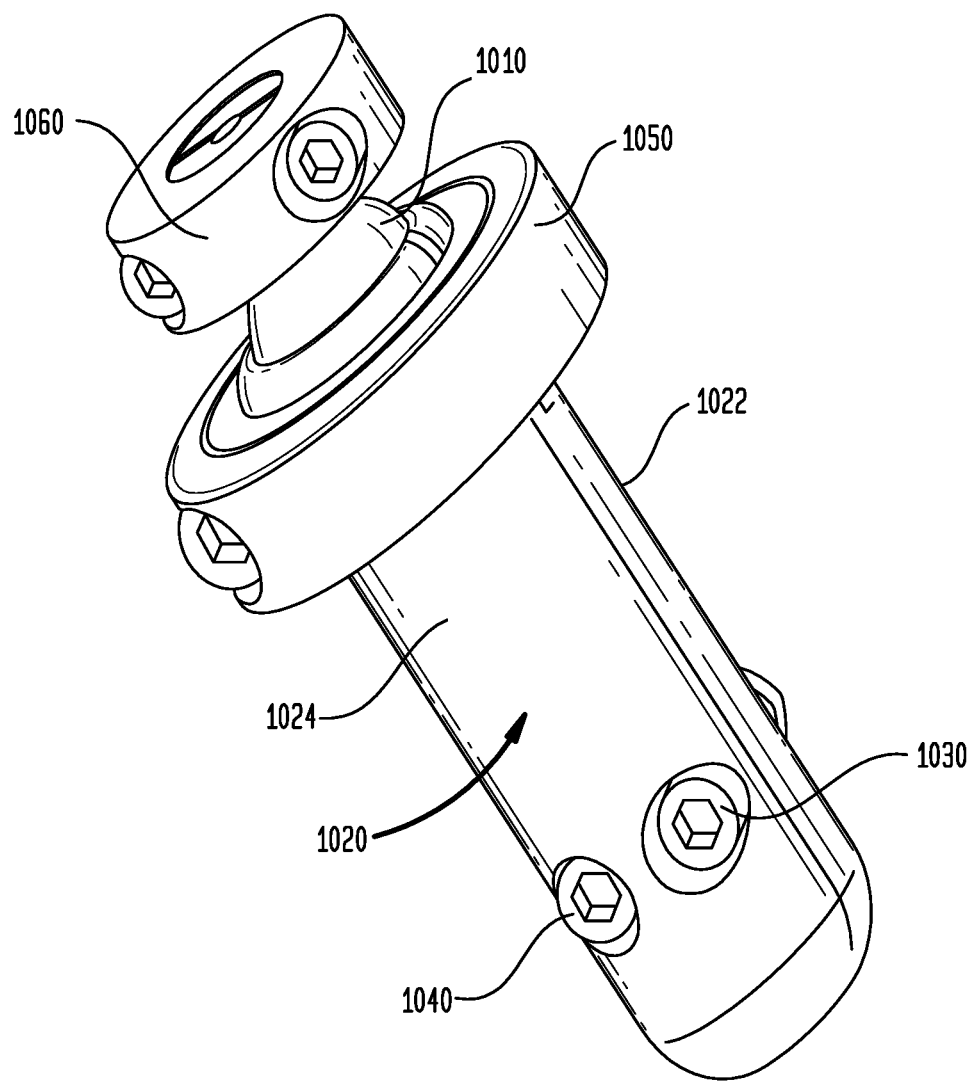
FIG. 10A is an enlarged perspective view of an actuator mechanism for manipulating control wires of an articulating assembly in accordance with the present disclosure.
Figure 10B:
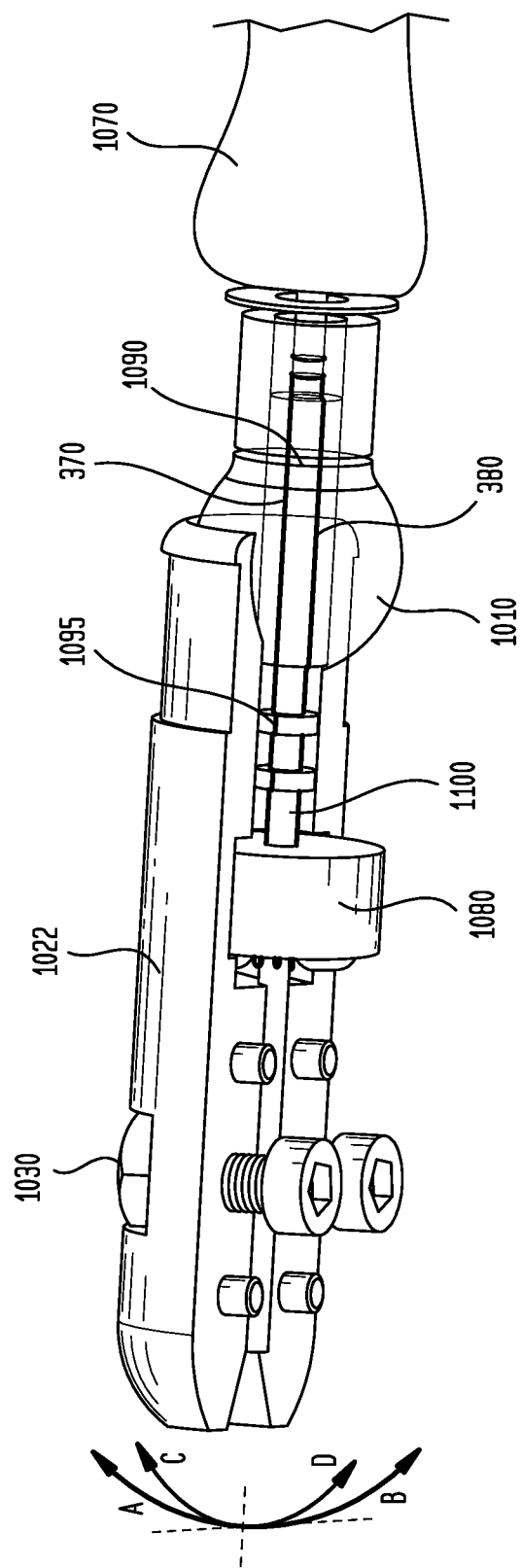
FIG. 10B is a perspective view of a half section of the actuator mechanism of FIG. 10A secured to a handle of the delivery system.
Figure 10C:
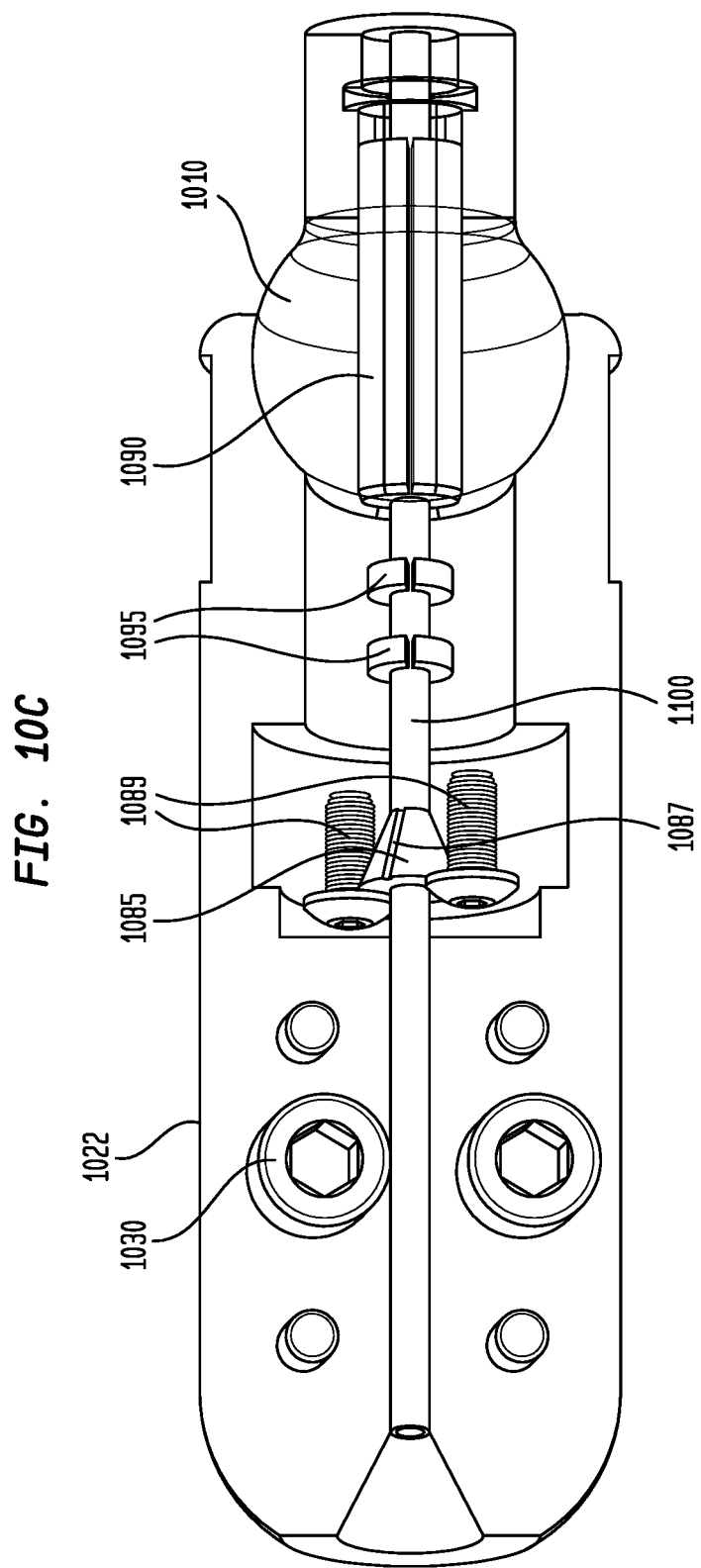
FIG. 10C is the perspective view of half section of the actuator mechanism of FIG. 10B with the anchor removed.
Figure 10D:
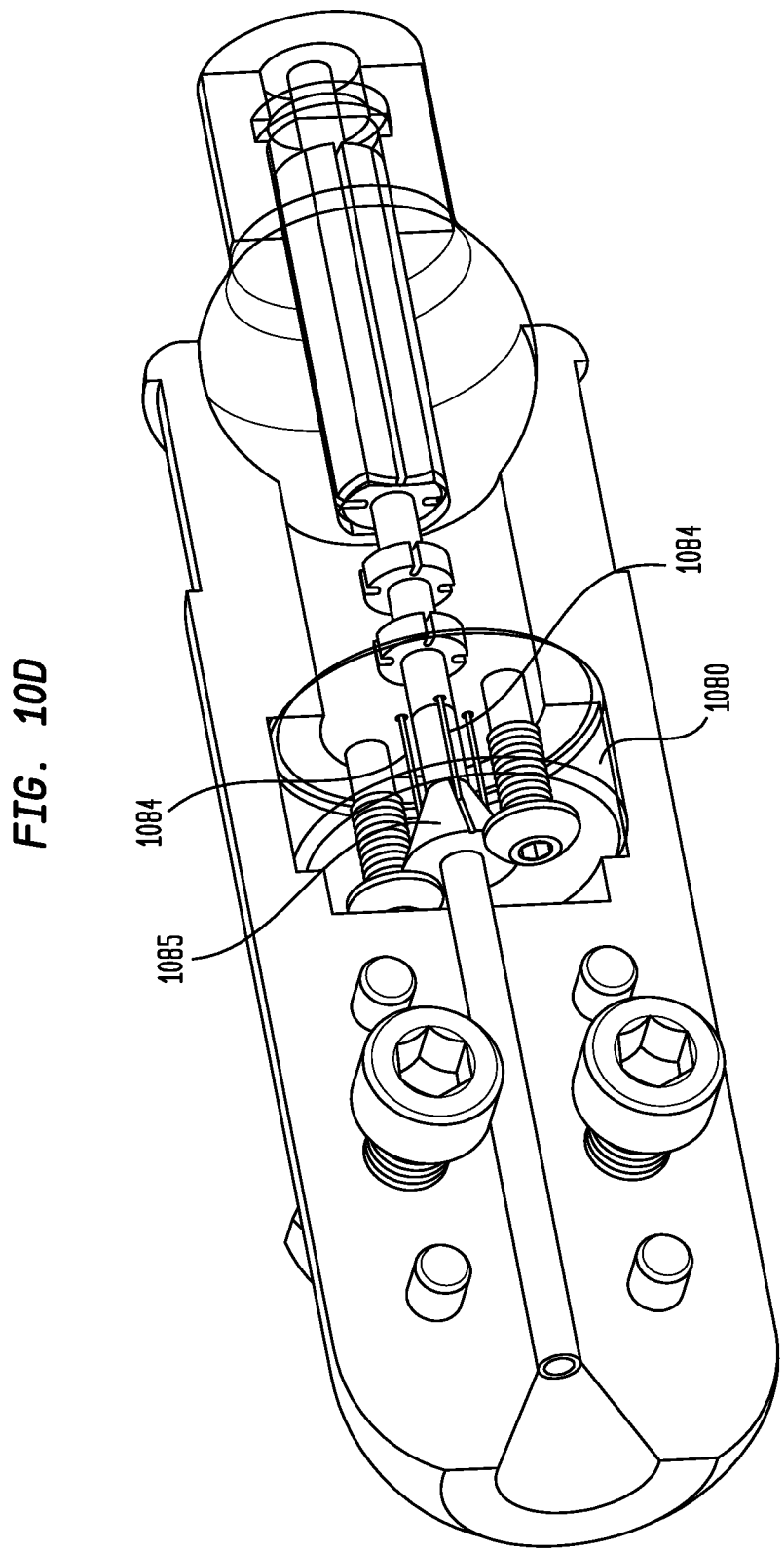
FIG. 10D is the perspective view of half section of the actuator mechanism of FIG. 10C with the anchor rendered transparent.

As can be seen in FIG. 10B, first and second control wires 370, 380 extend through handle 1070 and ball 1010 and are secured to an annular anchor 1080 held in place within complementary recesses formed in housing portions 1022, 1024. FIGS. 10C and 10D further illustrate an exemplary configuration for securing control wires 370, 380 to annular anchor 1080, with the annular anchor removed. Annular anchor 1080 includes a wedge 1085. In an exemplary embodiment, wedge 1085 has a generally conical body with slots 1087 defined thereon. Wedge 1085 is secured to anchor 1080 using a pair of set-screws 1089. A generally cylindrical insert 1090 and a shaft 1100 are longitudinally aligned with one another between handle 1070 and anchor 1080. First and second control wires 370, 380 are guided between handle 1070 and anchor 1080 by grooves formed in the outer surface of insert 1090 and by collinear grooves formed in two supports 1095 mounted on shaft 1100. Control wires 370, 370', 380, and 380' further extend through anchor 1080, along slots 1087 and are secured to wedge 1085 at their proximal ends. In an exemplary embodiment, the control wires 370, 370', 380, and 380' may be welded to wedge 1085 at their proximal ends. Four arrows A, B, C, D illustrate four principal directions in which housing 1020 may pivot relative to ball 1010 and handle 1070, with corresponding articulating movements of the support shaft, similar to the articulating movements described above.

Figure 11A:
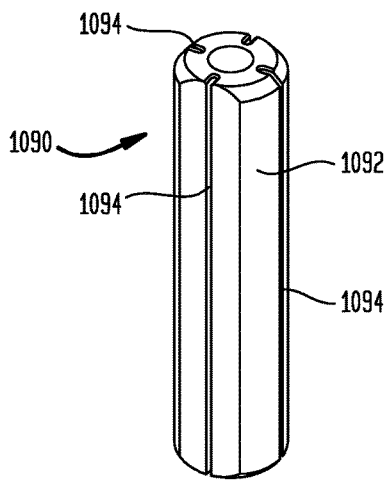
FIG. 11A is a perspective view of an insert for the control wires for use in the actuator mechanism of FIG. 10A.
Figure 11B:
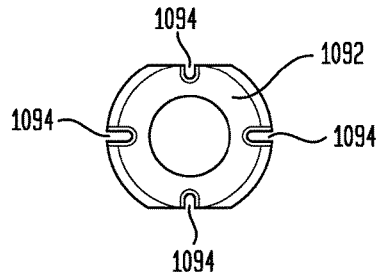
FIG. 11B is a top view of the insert of FIG. 11A.

FIG. 11A is a perspective view of insert 1090 and FIG. 11B a top view thereof. In the illustrated embodiment, insert 1090 has a generally cylindrical body 1092 with grooves 1094 formed longitudinally along the outer surface thereof. Each groove 1094 is configured to slidably accommodate a control wire, such as control wire 370 or 380. While the illustrated embodiment of insert 1090 includes four grooves 1094, it will be understood that the number of grooves may be more or less than four, depending on the number of control wires in the delivery system.

Figure 11C:
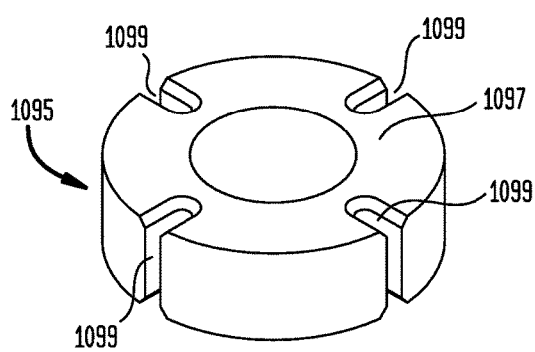
FIG. 11C is a perspective view of a support for the control wires for use in the actuator mechanism of FIG. 10A.
Figure 11D:
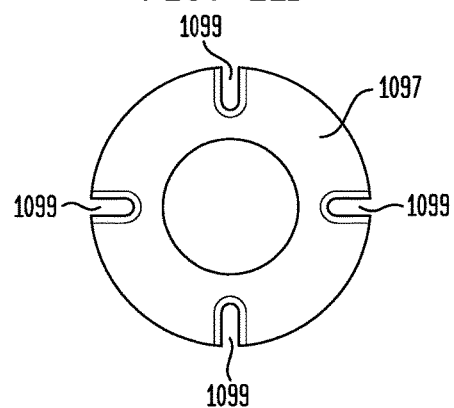
FIG. 11D is a top view of the support of FIG. 11C.

FIG. 11C is a perspective view of support 1095, and FIG. 11D is a top view of same. In the illustrated embodiment, support 1095 has a disc-like body 1097 with grooves 1099 formed longitudinally along the outer surface thereof. Each groove 1099 is configured to slidably accommodate one of the control wires of the delivery system. While the illustrated embodiment of support 1095 includes four grooves 1099, it will be understood that the number of grooves may be more than or less than four, depending on the number of control wires in the delivery system.

Figure 11E:
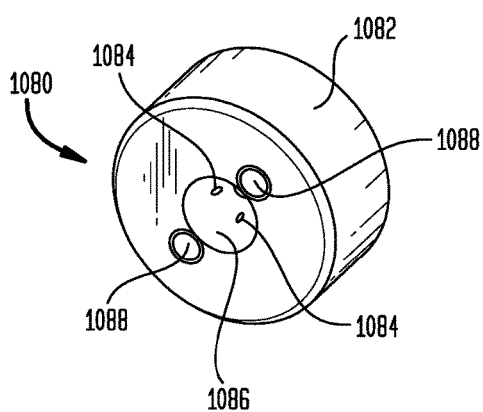
FIG. 11E is a perspective view of an anchor for the control wires for use in the actuator mechanism of FIG. 10A.
Figure 11F:
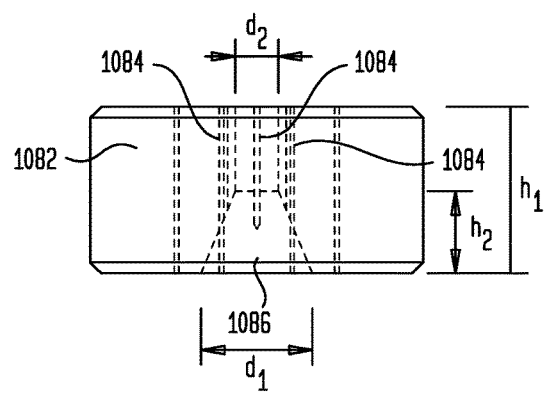
FIG. 11F is a side elevational view of the anchor of FIG. 11E.

FIG. 11E is a perspective view of anchor 1080 and FIG. 11F is a side elevational view thereof. Anchor 1080 has a disc-like body 1082 having a height $h_1$ with four apertures 1084 extending longitudinally therethrough. Each aperture 1084 is configured to accommodate one of the control wires through anchor 1080. A generally frusto-conical slot 1086 having a height $h_2$, a proximal diameter $d_1$ and a distal diameter $d_2$, is defined in anchor 1080 extending from a proximal end of disc-like body 1082 to an intermediate point. In an exemplary embodiment, the height $h_2$ may be about half of the height $h_1$. In the illustrated embodiment, two apertures 1088 are defined proximal to the conical slot 1086 and are configured to receive set screws 1089. While the illustrated embodiment of anchor 1080 includes four apertures 1084, it will be understood that the number of apertures may be more or less than four, depending on the number of control wires in the delivery system. Similarly, while the illustrated embodiment of anchor 1080 includes two apertures 1088, it will be understood that the number of apertures may be more or less than four, depending on the number of set screws used to secure wedge 1085 to the anchor. Still further, the dimensions of wedge 1085 and slot 1086 may be varied depending on the requirements of a given application.

Figure 11G:
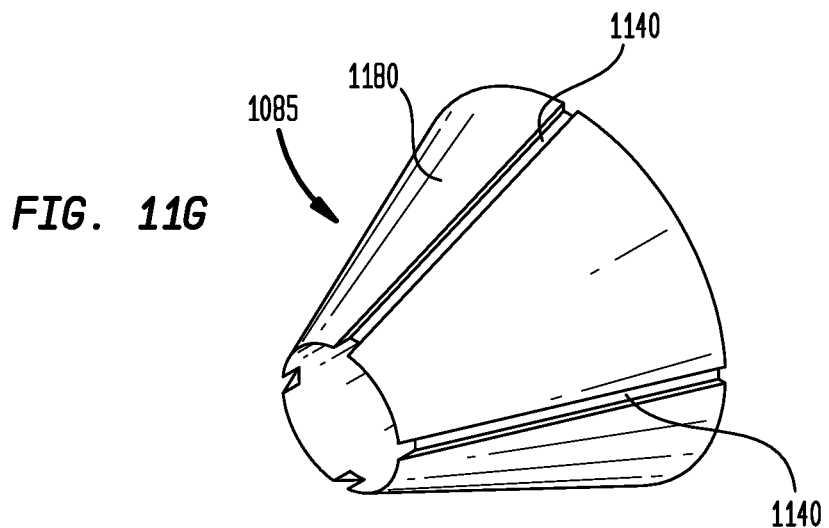
FIG. 11G is a perspective view of a wedge for securing the control wires to the anchor.
Figure 11H:
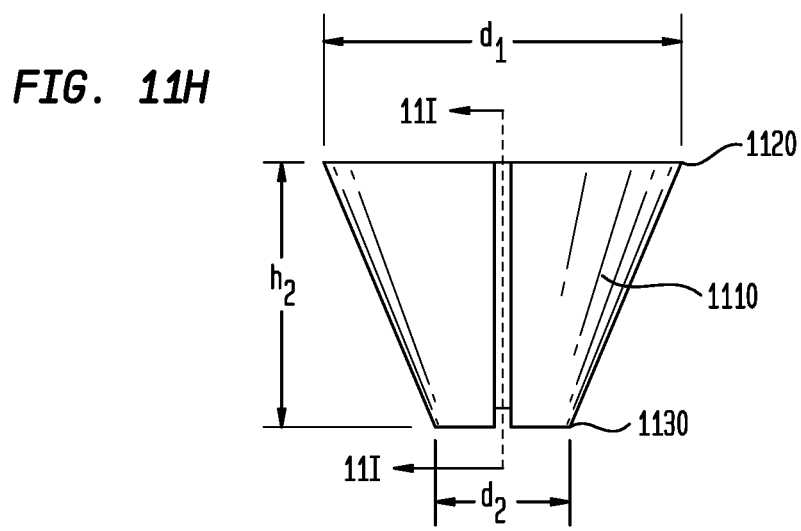
FIG. 11H is a side elevational view of the wedge of FIG. 11G.
Figure 11I:
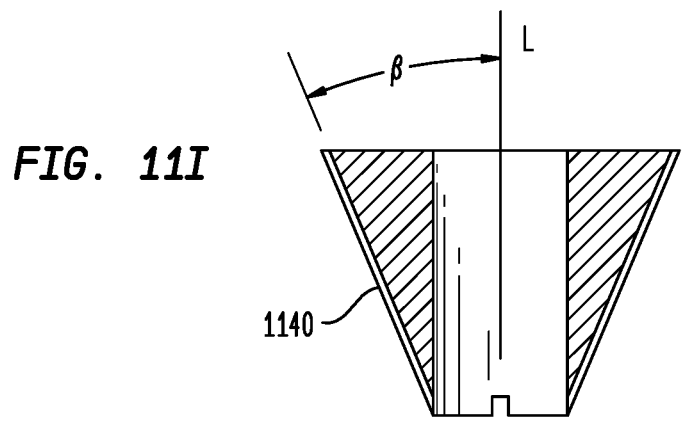
FIG. 11I is a cross-sectional view of the wedge of FIG. 11G.

FIG. 11G is a perspective view of wedge 1085, FIG. 11H is a side elevational view thereof, and FIG. 11I is a cross-section of wedge 1085 along line 11I. Wedge 1085 includes a generally frusto-conical body 1110 having a base 1120 and an apex 1130. The body has a proximal diameter $d_1$ at base 1120, a distal diameter $d_2$ at apex 1130, and a height $h_2$. Outer surface 1140 of body 1110 defines an angle β with the longitudinal axis L of body 1110. The dimensions of body 1110 generally correspond to those of frusto-conical slot 1086 in anchor 1180, thereby providing a snug fit between wedge 1085 and the anchor. In the illustrated embodiment, four longitudinal slots 1140 are defined in body 1110 to accommodate therewithin control wires 370, 370', 380, and 380'.

An embodiment of a medical device delivery system includes an inner shaft having a proximal end and a distal end, a support shaft having a proximal end and a distal end, the support shaft being sized for insertion into the circulatory system of a patient, and an articulating assembly disposed between the inner shaft and the support shaft, the articulating assembly including a first portion at the distal end of the inner shaft and a second portion at the proximal end of the support shaft, the first portion being pivotable relative to the second portion to change the orientation of the support shaft relative to the inner shaft; and/or the articulating assembly includes a plurality of control wires, movement of one of the control wires proximally causing the second portion of the articulating assembly to pivot relative to the first portion of the articulating assembly; and/or one of the first and second portions of the articulating assembly is a ball and another of the first and second portions of the articulating assembly is a socket sized to pivotably receive the ball; and/or the plurality of control wires includes four control wires secured to the second portion of the articulating assembly; and/or a first two of the control wires lies in a first plane and a second two of the control wires lies in a second plane perpendicular to the first plane; and/or the delivery system further includes a handle disposed proximally of the inner shaft, and an actuator assembly secured to the handle, the actuator assembly including a housing pivotably mounted to the handle, the plurality of control wires being secured to the housing so that a pivoting movement of the housing relative to the handle pulls at least one of the control wires proximally; and/or the delivery system includes an anchor for securing the plurality of control wires; and/or the delivery system includes a wedge mounted within the anchor for securing the plurality of control wires; and/or the wedge comprises a frustoconical body and the anchor includes a slot configured for accommodating the wedge; and/or the delivery system includes a retainer secured to the second portion of the articulating assembly and configured to retain a medical device on the support shaft; and/or the delivery system includes a distal outer sheath configured to cover the inner shaft and the support shaft in a first condition, and movable to a second condition exposing the support shaft, and a proximal outer sheath configured to cover the inner shaft; and/or the delivery system includes a constricting element mounted on the inner shaft and comprising a generally cylindrical portion and an outwardly flaring portion facing the articulating assembly; and/or the outwardly flaring portion has a diameter greater than a diameter of the proximal outer sheath; and/or the inner shaft includes a plurality of notches proximal to the distal end; and/or one of the first and second portions of the articulating assembly includes a generally concave bearing surface and another of the first and second portions of the articulating assembly includes a ball pivotably engaging the bearing surface, and the delivery system further includes a sheath covering the first and second portions of the articulating assembly and longitudinally constraining the ball relative to the bearing surface.

Another embodiment of the present disclosure includes a medical device delivery system including a support shaft configured to retain a medical device in a collapsed condition and having a proximal end and a distal end, an inner shaft having a proximal end and a distal end, an articulating assembly disposed between the support shaft and the inner shaft, a handle disposed proximally of the inner shaft, an actuator mechanism pivotably secured to the handle, and a plurality of control wires operatively interconnecting the articulating assembly and the actuator mechanism such that pivoting movement of the actuator mechanism causes a corresponding pivoting movement of the support shaft relative to the inner shaft; and/or the articulating assembly includes a ball pivotably engaged in a socket; and/or the ball is at the distal end of the inner shaft and the socket is at the proximal end of the support shaft; and/or the plurality of control wires have first ends secured to the socket; and/or the delivery system includes a distal outer sheath and a proximal outer sheath for covering the inner shaft, the articulating assembly and the support shaft.

Although the present disclosure has been made with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the present claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A medical device delivery system, comprising:
an inner shaft having a proximal end and a distal end;
a support shaft having a proximal end, a distal end and a distal tip at the distal end, the support shaft being sized for insertion into the circulatory system of a patient;
an articulating assembly disposed between the inner shaft and the support shaft, the articulating assembly including a first portion extending from the distal end of the inner shaft and a second portion at the proximal end of the support shaft, the first portion being pivotable relative to the second portion to change the orientation of the support shaft relative to the inner shaft, and
a retainer secured to the second portion of the articulating assembly,
wherein the support shaft extends distally from the retainer to the distal tip so as to support a medical device thereupon between the retainer and the distal tip.

2. The delivery system of claim 1, wherein the articulating assembly includes a plurality of control wires, movement of one of the control wires proximally causing the second portion of the articulating assembly to pivot relative to the first portion of the articulating assembly.

3. The delivery system of claim 2, wherein one of the first and second portions of the articulating assembly is a ball and another of the first and second portions of the articulating assembly is a socket sized to pivotably receive the ball.

4. The delivery system of claim 2, wherein the plurality of control wires includes four control wires secured to the second portion of the articulating assembly.

5. The delivery system of claim 4, wherein a first two of the control wires lies in a first plane and a second two of the control wires lies in a second plane perpendicular to the first plane.

6. The delivery system of claim 2, further comprising:
a handle disposed proximally of the inner shaft; and
an actuator assembly secured to the handle, the actuator assembly including a housing pivotably mounted to the handle, the plurality of control wires being secured to the housing so that a pivoting movement of the housing relative to the handle pulls at least one of the control wires proximally.

7. The delivery system of claim 6, further comprising an anchor for securing the plurality of control wires.

8. The delivery system of claim 7, further comprising a wedge mounted within the anchor for securing the plurality of control wires.

9. The delivery system of claim 8, wherein the wedge comprises a frustoconical body and the anchor includes a slot configured for accommodating the wedge.

10. The delivery system of claim 1, further comprising a distal outer sheath configured to cover the inner shaft and the support shaft in a first condition, and movable to a second condition exposing the support shaft; and
a proximal outer sheath configured to cover the inner shaft.

11. The delivery system of claim 10, further comprising a constricting element mounted on the inner shaft and comprising a generally cylindrical portion and an outwardly flaring portion facing the articulating assembly.

12. The delivery system of claim 11, wherein the outwardly flaring portion has a diameter greater than a diameter of the proximal outer sheath.

13. The delivery system of claim 1, wherein the inner shaft includes a plurality of notches proximal to the distal end.

14. The delivery system of claim 1, wherein one of the first and second portions of the articulating assembly includes a generally concave bearing surface and another of the first and second portions of the articulating assembly includes a ball pivotably engaging the bearing surface,
the delivery system further including a sheath covering the first and second portions of the articulating assembly and longitudinally constraining the ball relative to the bearing surface.

15. The delivery system of claim 1, wherein the support shaft has a first diameter and the retainer has a second diameter greater than the first diameter.

16. A medical device delivery system, comprising:
a support shaft having a proximal end, a distal end and a conically shaped distal tip at the distal end;
an inner shaft having a proximal end and a distal end;
an articulating assembly disposed between the support shaft and the inner shaft;
a retainer secured to a portion of the articulating assembly, wherein the support shaft extends distally from the retainer to the conically shaped distal tip so as to support a medical device in a collapsed condition thereupon between the retainer and the conically shaped distal tip;
a handle disposed proximally of the inner shaft;
an actuator mechanism pivotably secured to the handle; and
a plurality of control wires operatively interconnecting the articulating assembly and the actuator mechanism such that pivoting movement of the actuator mechanism causes a corresponding pivoting movement of the support shaft relative to the inner shaft.

17. The delivery system of claim 16, wherein the articulating assembly includes a ball pivotably engaged in a socket.

18. The delivery system of claim 17, wherein the ball is at the distal end of the inner shaft and the socket is at the proximal end of the support shaft.

19. The delivery system of claim 18, wherein the plurality of control wires have first ends secured to the socket.

20. The delivery system of claim 16, further comprising a distal outer sheath and a proximal outer sheath for covering the inner shaft, the articulating assembly and the support shaft.

* * * * *